(12) United States Patent
Yamauchi

(10) Patent No.: US 7,173,704 B2
(45) Date of Patent: Feb. 6, 2007

(54) MEASURING DEVICE FOR IMMUNOCHROMATOGRAPHY TEST PIECE AND LIGHT SOURCE DEVICE

(75) Inventor: Kazunori Yamauchi, Hamamatsu (JP)

(73) Assignee: Hamamatsu Photonics K.K., Shizuoka (JP)

( * ) Notice: Subject to any disclaimer, the term of this patent is extended or adjusted under 35 U.S.C. 154(b) by 429 days.

(21) Appl. No.: 10/785,411

(22) Filed: Feb. 25, 2004

(65) Prior Publication Data
US 2005/0036914 A1   Feb. 17, 2005

(30) Foreign Application Priority Data
Feb. 26, 2003   (JP) .............................. 2003-049913

(51) Int. Cl.
*G01N 21/00* (2006.01)
(52) U.S. Cl. ...................... 356/432; 356/318; 356/344; 422/56; 422/82.05
(58) Field of Classification Search ........ 356/432–444, 356/326, 318–319, 71–72, 344; 250/227; 422/56–57, 68, 82.05
See application file for complete search history.

(56) References Cited

U.S. PATENT DOCUMENTS

| | | | | |
|---|---|---|---|---|
| 3,700,333 A | * | 10/1972 | Charlson et al. ............ | 356/339 |
| 4,310,249 A | * | 1/1982 | Kramer ....................... | 356/414 |
| 4,632,559 A | * | 12/1986 | Brunsting ................... | 356/416 |
| 4,676,653 A | * | 6/1987 | Strohmeier et al. ......... | 356/446 |
| 4,930,865 A | * | 6/1990 | Dosmann .................... | 359/629 |
| 5,028,139 A | * | 7/1991 | Kramer et al. .............. | 356/446 |
| 5,654,803 A | | 8/1997 | Howard, III et al. ....... | 356/446 |
| 6,819,422 B2 | * | 11/2004 | Yamauchi ................... | 356/344 |

FOREIGN PATENT DOCUMENTS

| | | |
|---|---|---|
| EP | 1249696 A1 * | 10/2002 |
| JP | 61-262635 | 11/1986 |
| JP | 07-005110 | 1/1995 |
| JP | 8-094475 | 4/1996 |
| JP | 10-10123 | 1/1998 |
| JP | 11-083745 | 3/1999 |
| JP | 11-142338 | 5/1999 |
| JP | 11-242150 | 9/1999 |
| JP | 11-326191 | 11/1999 |
| JP | 2001-296246 A | 10/2001 |
| JP | 2002-098631 | 4/2002 |
| JP | 2002-098631 A | 4/2002 |

* cited by examiner

*Primary Examiner*—Sang H. Nguyen
(74) *Attorney, Agent, or Firm*—Drinker Biddle & Reath LLP

(57) ABSTRACT

A measuring device for immunochromatography test piece comprising an irradiation optical system for irradiating measurement light onto an immunochromatography test piece, and a detection optical system for detecting reflected light from the immunochromatography test piece under irradiation with the measurement light. The irradiation optical system comprises a semiconductor light emitting element, a beam shaping member, a lens, a first baffle portion, a second baffle portion, and a third baffle portion. The beam shaping member shapes light from the semiconductor light emitting element, into a beam of a beam section extending in a direction substantially parallel to a colored line formed on the immunochromatography test piece. The lens focuses the beam from the beam shaping member on the immunochromatography test piece. The first baffle portion removes stray light, which is disposed between the semiconductor light emitting element and the beam shaping member. The second baffle portion removes stray light, which is disposed between the beam shaping member and the lens. The third baffle portion removes stray light, which is disposed between the lens and the immunochromatography test piece.

16 Claims, 14 Drawing Sheets

MEASURING DEVICE FOR IMMUNOCHROMATOGRAPHY TEST PIECE AND LIGHT SOURCE DEVICE

BACKGROUND OF THE INVENTION

1. Field of the Invention

The present invention relates to a measuring device for immunochromatography test piece, and a light source device.

2. Related Background Art

An immunochromatography test piece is a test piece preliminarily coated with a bandlike coating of an antibody (or antigen) which brings about an antigen-antibody reaction with an antigen (or antibody) in analyte, at a specific location of the test piece. When the antigen (or antibody) in analyte labeled with a dye is developed to the aforementioned specific location by a developing solution, the antigen (or antibody) in analyte undergoes the antigen-antibody reaction with the bandlike coating of the antigen (or antibody) to be trapped, forming a colored line of color by the dye at the specific location. With the immunochromatography test piece of this type, the amount of the antigen (or antibody) in analyte can be quantitatively determined by optically measuring the color intensity of the colored line thus formed, by means of a measuring device.

As a device for measuring the color intensity of the test piece such as the immunochromatography test piece, there is a known measuring device configured to irradiate measurement light of a beam section extending in a direction (a direction parallel to the colored line) perpendicular to the sample development direction on the immunochromatography test piece (the moving direction of the antigen or antibody on the immunochromatography test piece) and to detect reflected light from the immunochromatography test piece under irradiation with the measurement light (e.g., cf. Patent Document 1). The measuring device described in this Patent Document 1 is provided with a laser diode as a light source, and light from the laser diode is guided through a focusing lens and a slit to obtain the foregoing measurement light.

[Patent Document 1] Japanese Patent Application Laid-Open No. 11-326191

SUMMARY OF THE INVENTION

However, the measuring device disclosed in above Patent Document 1 involves generation of stray light and has a problem that the stray light results in losing clearness (sharpness) of the measuring light focused on the immunochromatography test piece and, in turn, degrading the measurement accuracy of color intensity. The degradation of measurement accuracy due to the generation of stray light becomes prominent, particularly, where the intensity of light from the light source is increased.

The present invention has been accomplished in view of the foregoing point and a first object of the invention is to provide a measuring device for immunochromatography test piece capable of suppressing the generation of stray light and thereby improving the measurement accuracy of color intensity.

A second object of the present invention is to provide a light source device capable of suppressing the generation of stray light and emitting sharp slit light.

In order to achieve the above object, a measuring device for immunochromatography test piece according to the present invention is a measuring device for immunochromatography test piece comprising an irradiation optical system for irradiating measurement light onto an immunochromatography test piece, and a detection optical system for detecting reflected light from the immunochromatography test piece under irradiation with the measurement light, wherein the irradiation optical system comprises: a semiconductor light emitting element; a beam shaping member for shaping light from the semiconductor light emitting element, into a beam of a beam section extending in a direction substantially parallel to a colored line formed on the immunochromatography test piece; a lens for focusing the beam from the beam shaping member on the immunochromatography test piece; a first baffle portion of tubular shape for removing stray light, which is disposed between the semiconductor light emitting element and the beam shaping member; a second baffle portion of tubular shape for removing stray light, which is disposed between the beam shaping member and the lens; and a third baffle portion of tubular shape for removing stray light, which is disposed between the lens and the immunochromatography test piece.

In the measuring device for immunochromatography test piece according to the present invention, the first baffle portion is disposed between the semiconductor light emitting element and the beam shaping member, the second baffle portion between the beam shaping member and the lens, and the third baffle portion between the lens and the immunochromatography test piece; therefore, these baffle portions of tubular shape suppress the generation of stray light well. The lens focuses the beam from the beam shaping member on the immunochromatography test piece. These prevent unwanted stray light from entering the immunochromatography test piece, so as to sharpen the measurement light projected onto the immunochromatography test piece, whereby it becomes feasible to achieve significant improvement in the measurement accuracy of color intensity.

Preferably, the irradiation optical system further comprises a tubular space portion with a diameter larger than that of the first baffle portion, which is disposed between the first baffle portion and the beam shaping member. In this case, stray light is confined in the tubular space portion, and it can suppress the incidence of unwanted stray light to the immunochromatography test piece all the more.

Preferably, the irradiation optical system further comprises a tubular space portion with a diameter larger than that of the second baffle portion, which is disposed between the beam shaping member and the second baffle portion. In this case, stray light is confined in the tubular space portion, and it can suppress the incidence of unwanted stray light to the immunochromatography test piece all the more.

Preferably, the irradiation optical system further comprises a tubular space portion with a diameter larger than that of the third baffle portion, which is disposed between the lens and the third baffle portion. In this case, stray light is confined in the tubular space portion, and it can suppress the incidence of unwanted stray light to the immunochromatography test piece all the more.

Preferably, the irradiation optical system is mounted on an optical head, the optical head comprising: a first member comprising a first hole portion, a second hole portion, a third hole portion, a fourth hole portion, and a fifth hole portion continuously formed, wherein the first hole portion has a predetermined inside diameter so as to function as the third baffle portion, the second hole portion has an inside diameter larger than that of the first hole portion, the third hole portion has an inside diameter larger than that of the second hole portion and allows the lens to be inserted therein, the fourth hole portion has an inside diameter larger than that of the third hole portion, and the fifth hole portion has an inside diameter larger than that of the fourth hole portion; a second member inserted in the fifth hole portion and comprising a sixth hole portion and a seventh hole portion continuously formed, wherein the sixth hole portion allows the semiconductor light emitting element to be inserted therein and the seventh hole portion has a predetermined inside diameter so as to function as the first baffle portion; and a tubular member inserted in the fourth hole portion and having a predetermined inside diameter so that a one-end portion functions as the second baffle portion; the lens is fixed by the tubular member and a step portion formed at a border portion between the second hole portion and the third hole portion; and the beam shaping member is fixed by the second member and a step portion formed at a border portion between the fourth hole portion and the fifth hole portion. In this case, the irradiation optical system (semiconductor light emitting element, beam shaping member, lens, first baffle portion, second baffle portion, and third baffle portion) can be built in the optical head to be unitized, which simplifies the structure and which facilitates assembly of the semiconductor light emitting element, beam shaping member, and lens.

Preferably, in the second member, an eighth hole portion having an inside diameter larger than that of the seventh hole portion is formed so as to be continuous with the seventh hole portion. In this case, stray light is confined in the space portion defined by the eighth hole portion, which enables the device to further suppress the incidence of unwanted stray light to the immunochromatography test piece.

Preferably, the tubular member comprises an other-end portion having an inside diameter set larger than the inside diameter of the one-end portion. In this case, stray light is confined in the space portion defined by the other-end portion in the tubular member, which enables the device to further suppress the incidence of unwanted stray light to the immunochromatography test piece.

Preferably, a female screw is threaded in each inside surface of the first hole portion, the seventh hole portion, and the one-end portion of the tubular member. In this case, by the extremely simple configuration wherein a female screw is threaded, it is feasible to further effectively suppress the incidence of unwanted stray light to the immunochromatography test piece.

Preferably, the measuring device further comprises an optical head on which the irradiation optical system and the detection optical system are mounted; a placing plate for placing of the immunochromatography test piece; and a scanning mechanism for effecting relative movement between the placing plate and the optical head in a scan direction traversing the colored line. In this case, the irradiation optical system and the detection optical system are mounted on the optical head, which simplifies the structure and which requires only one system as a scanning mechanism for moving the optical head in the scan direction, thus simplifying the structure of the scanning mechanism and a configuration of a control system thereof.

Preferably, the semiconductor light emitting element is a light emitting diode. In this case, the intensity of light from the light source can be increased.

Preferably, the beam shaping member is a platelike member in which a slit extending in a direction substantially parallel to the colored line formed on the immunochromatography test piece is formed. In this case, the structure of the beam shaping member can be simplified.

In order to achieve the above object, a light source device according to the present invention is a light source device for irradiating slit light onto a measuring object, comprising: a semiconductor light emitting element; a beam shaping member for shaping light from the semiconductor light emitting element, into a slit beam; a lens for focusing the beam from the beam shaping member on the measuring object; a first baffle portion of tubular shape for removing stray light, which is disposed between the semiconductor light emitting element and the beam shaping member; a second baffle portion of tubular shape for removing stray light, which is disposed between the beam shaping member and the lens; and a third baffle portion of tubular shape for removing stray light, which is disposed between the lens and the measuring object.

In the light source device according to the present invention, the first baffle portion is disposed between the semiconductor light emitting element and the beam shaping member, the second baffle portion between the beam shaping member and the lens, and the third baffle portion between the lens and the immunochromatography test piece; therefore, these baffle portions of tubular shape suppress the generation of stray light well. The lens focuses the slit beam from the beam shaping member on the measuring object. These prevent unwanted stray light from entering the measuring object, so as to sharpen the slit beam projected onto the measuring object.

Preferably, the light source device further comprises a tubular space portion with a diameter larger than that of the first baffle portion, which is disposed between the first baffle portion and the beam shaping member. In this case, stray light is confined in the tubular space portion, which enables the device to further suppress the incidence of unwanted stray light to the measuring object.

Preferably, the light source device further comprises a tubular space portion with a diameter larger than that of the second baffle portion, which is disposed between the beam shaping member and the second baffle portion. In this case, stray light is confined in the tubular space portion, which enables the device to further suppress the incidence of unwanted stray light to the measuring object.

Preferably, the light source device further comprises a tubular space portion with a diameter larger than that of the third baffle portion, which is disposed between the lens and the third baffle portion. In this case, stray light is confined in the tubular space portion, which enables the device to further suppress the incidence of unwanted stray light to the measuring object.

In order to achieve the above object, another measuring device for immunochromatography test piece according to the present invention is a measuring device for immunochromatography test piece, comprising: a pedestal on which an immunochromatography test piece is placed; an irradiation optical system for irradiating measurement light toward the pedestal; and a detection optical system for detecting light incident from the pedestal side, wherein the irradiation optical system and the detection optical system are arranged to move relative to the pedestal in a predetermined scan direction, and wherein the irradiation optical system comprises: a semiconductor light emitting element; a beam shaping member for shaping light from the semiconductor light emitting element, into a beam of a beam section extending in a direction crossing the predetermined scan direction; a lens for focusing the beam from the beam shaping member; a first baffle portion of tubular shape for removing stray light, which is disposed between the semiconductor light emitting element and the beam shaping member; a second baffle portion of tubular shape for removing stray light, which is disposed between the beam shaping member and the lens; and a third baffle portion of tubular shape for removing stray light, which is disposed between the lens and the pedestal.

In the measuring device for immunochromatography test piece according to the present invention, unwanted stray light is prevented from entering the immunochromatography test piece, so as to sharpen the measurement light on the immunochromatography test piece, and it is feasible to achieve significant improvement in the measurement accuracy of color intensity.

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

Preferred embodiments of the measuring device for immunochromatography test piece according to the present invention will be described below in detail with reference to the drawings. In the description the same elements or elements having the same functions will be denoted by the same reference symbols, without redundant description. The measuring device for immunochromatography test piece according to the present embodiment incorporates a light source device according to an embodiment of the present invention.

Figure 1:
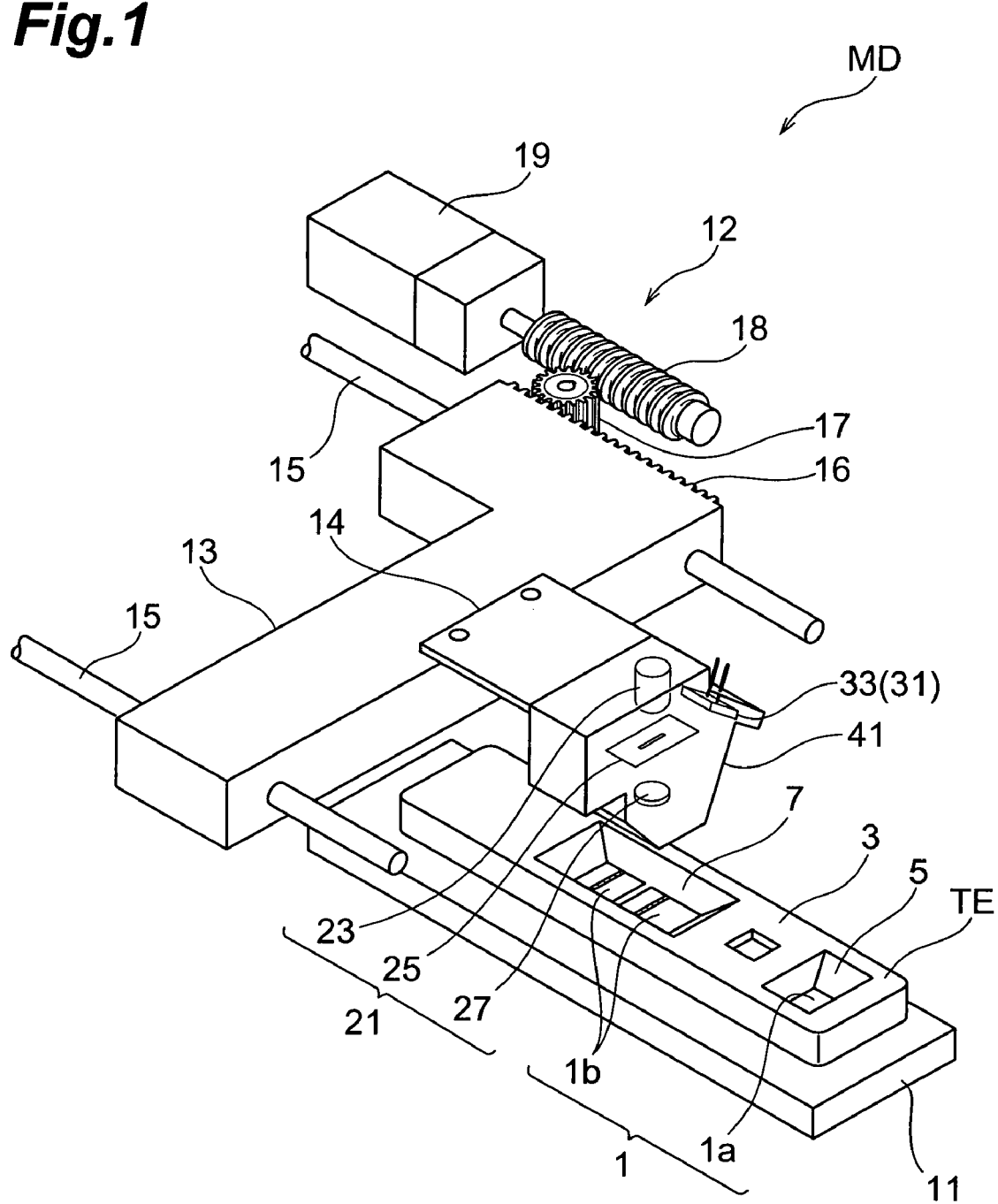
FIG. 1 is a perspective view showing a measuring device for immunochromatography test piece according to an embodiment of the invention.
Figure 2:
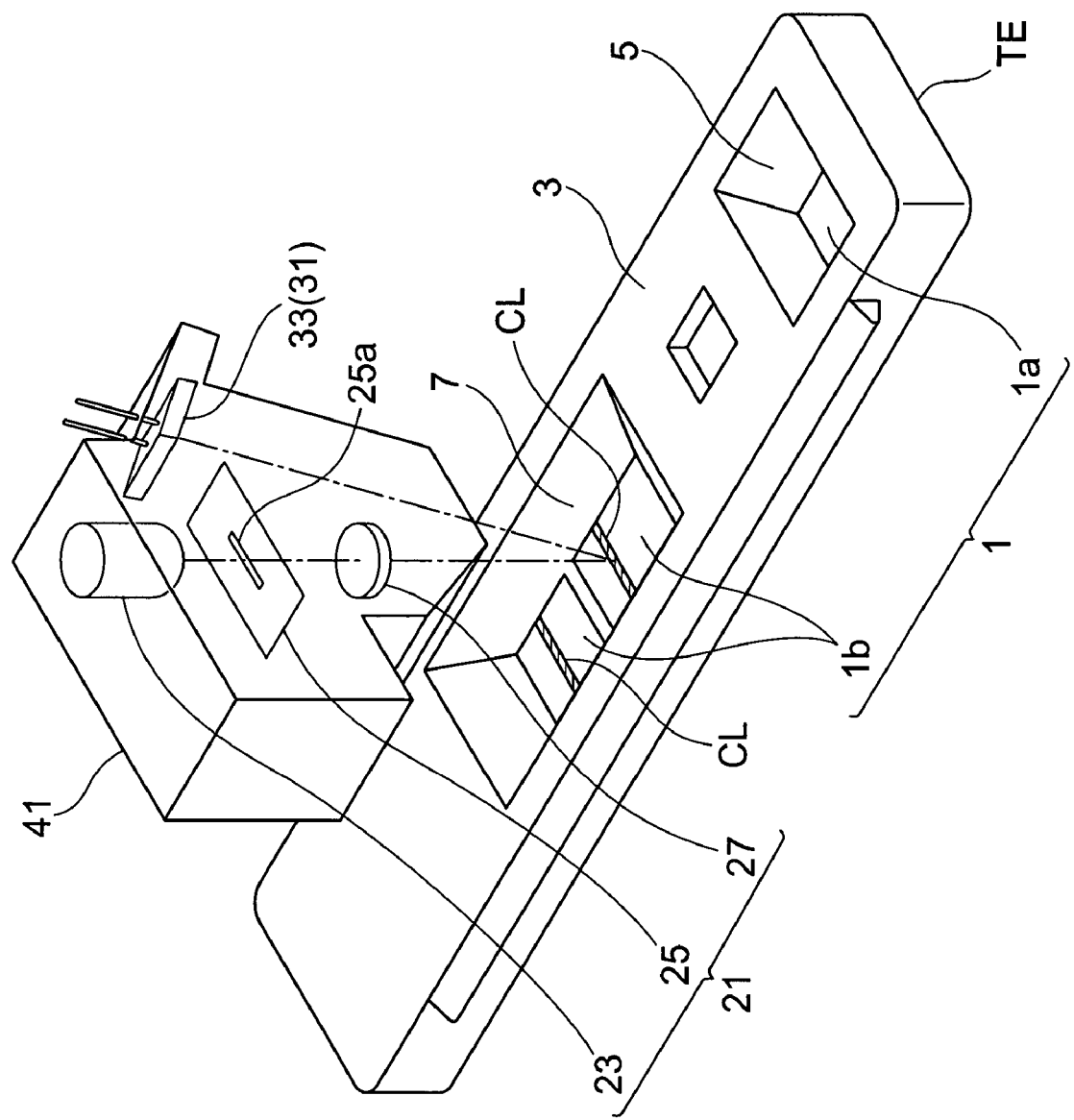
FIG. 2 is a perspective view of an optical head and immunochromatography test equipment shown in FIG. 1.

FIG. 1 is a perspective view showing the measuring device for immunochromatography test piece according to the present embodiment, and FIG. 2 a perspective view of the optical head and immunochromatography test equipment shown in FIG. 1. The measuring device MD of the present embodiment is a device that irradiates measurement light onto a colored line CL formed on an immunochromatography test piece 1 and that receives reflected light therefrom to measure the color intensity of the colored line CL. This measuring device MD, as shown in FIG. 1, has a placing plate 11 as a pedestal on which the immunochromatography test equipment TE is placed, an optical head 41 on which an irradiation optical system 21 and a detection optical system 31 are mounted, and a scanning mechanism 12 for moving the optical head 41 relative to the placing plate 11 in the scan direction. The irradiation optical system 21 irradiates light toward the placing plate 11, whereby measurement light is projected onto the immunochromatography test piece 1 placed on the placing plate 11. The detection optical system 31 receives light incident from the placing plate 11 side to detect reflected light from the immunochromatography test piece 1.

Figure 3:
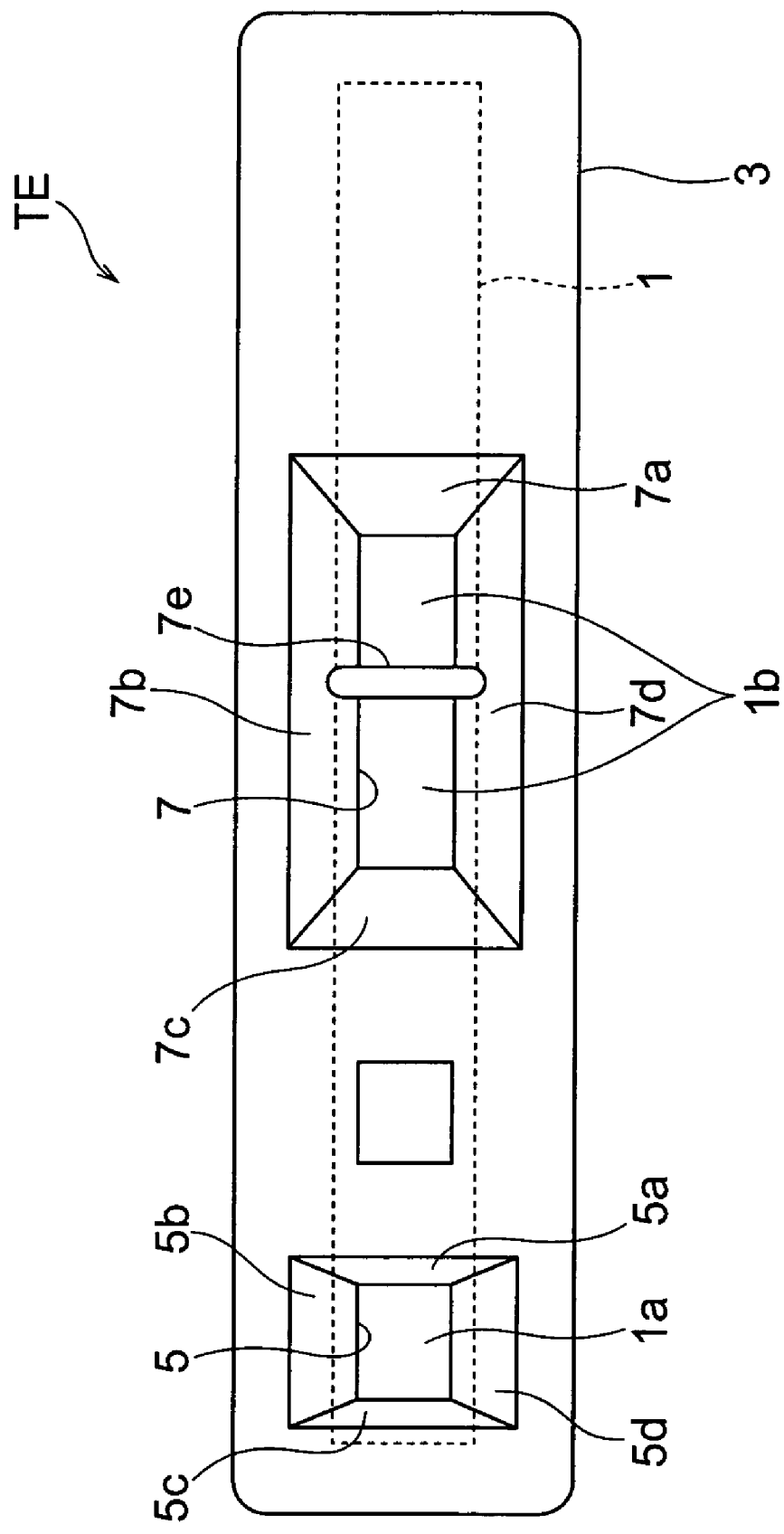
FIG. 3 is a plan view of an immunochromatography test equipment to be measured by the measuring device for immunochromatography test piece according to the embodiment.

Here the immunochromatography test equipment TE, as also shown in FIG. 3, has a casing 3 of rectangular shape on the plan view, and an immunochromatography test piece 1 held in the casing 3. FIG. 3 is a plan view of the immunochromatography test equipment.

The casing 3 is provided with an analyte drop window 5 for dropping an analyte, and an observation window 7 for exposing a colored portion of the immunochromatography test piece 1. Edges 5a–5d forming the analyte drop window 5 and edges 7a–7d forming the observation window 7 are inclined toward the immunochromatography test piece 1 so as to be formed in taper shape. In the immunochromatography test equipment TE of the present embodiment, a part of the observation window 7 is divided by a partition 7e, and is used as a control window.

The immunochromatography test piece 1 is made of a nitrocellulose membrane, filter paper, or the like and in rectangular shape. The immunochromatography test piece 1 has an analyte drop portion 1a provided at a position corresponding to the analyte drop window 5, and a detection portion 1b provided at a position corresponding to the observation window 7. The detection portion 1b is coated with antibodies (or antigens) that react with respective partner antigens (or antibodies) in analyte, the antibodies (or antigens) being immobilized in line shape (or band shape).

An analyte is delivered dropwise through the analyte drop window 5 onto the analyte drop portion 1a of the immunochromatography test piece 1. An antigen (or antibody) in the analyte binds to a label dye, and the combination of the antigen (or antibody) in the analyte with the label dye, and the non-reacted label dye move in the longitudinal direction of the immunochromatography test piece 1. Let us suppose that the analyte contains an antigen and the antigen brings about an antigen-antibody reaction with a partner antibody in the detection portion 1b. As the analyte moves, the antigen in the analyte specifically reacts with the partner antibody immobilized in the detection portion 1b to form a pattern of line shape (colored line CL) colored by the label dye in the detection portion 1b subject to reaction. This colored line CL is formed as extending in a direction (e.g., a perpendicular direction) crossing the moving direction of the antigen (or antibody) in the analyte on the immunochromatography test piece 1, and can be observed through the observation window 7. The colored line CL normally has the width of approximately 1.0 mm. The colored line CL normally has the longitudinal length of approximately 5 mm.

The irradiation optical system 21, as shown in FIGS. 1 and 2, has a semiconductor light emitting element 23, a beam shaping member 25, and a lens 27, and these semiconductor light emitting element 23, beam shaping member 25, and lens 27 are mounted on the optical head 41. In the present embodiment, a light emitting diode (LED) is used as the semiconductor light emitting element 23 and specifications of the light emitting diode are set to the center wavelength of 530 nm, the luminance of 3000 mc, and the directivity of 20°.

The beam shaping member 25 is a platelike member for shaping light from the semiconductor light emitting element 23 into a beam of a beam section extending in a direction nearly parallel to the colored line CL formed on the immunochromatography test piece 1, i.e., in a direction crossing the scan direction of the optical head 41 (in the present embodiment, the beam section extends in the direction perpendicular to the scan direction of optical head 41), and a slit 25a is formed in the platelike member. The shape of the slit 25a is set to be a rectangular shape (e.g., 50 μm in width and 3 mm in length). The extending direction of the slit 25a is set to be nearly parallel to the colored line CL formed on the immunochromatography test piece 1 in the immunochromatography test equipment TE placed on the placing plate 11, in a state in which the beam shaping member 25 is mounted on the optical head 41. By this, the light from the semiconductor light emitting element 23 is made to be a slit beam nearly parallel to the colored line CL formed on the immunochromatography test piece 1.

The lens 27 is provided for focusing the beam from the beam shaping member 25 (the slit beam nearly parallel to the colored line CL formed on the immunochromatography test piece 1), on the immunochromatography test piece 1 in the immunochromatography test equipment TE placed on the placing plate 11. In the present embodiment, the focal length of the lens 27 is set to 6 mm, and the size of a slit light image focused on the immunochromatography test piece 1 is 50 μm in width and 3 mm in length.

The detection optical system 31, as shown in FIGS. 1 and 2, has a semiconductor photodetector 33, and this semiconductor photodetector 33 is mounted on the optical head 41. In the present embodiment, a silicon (Si) photodiode is used as the semiconductor photodetector 33.

Figure 4:
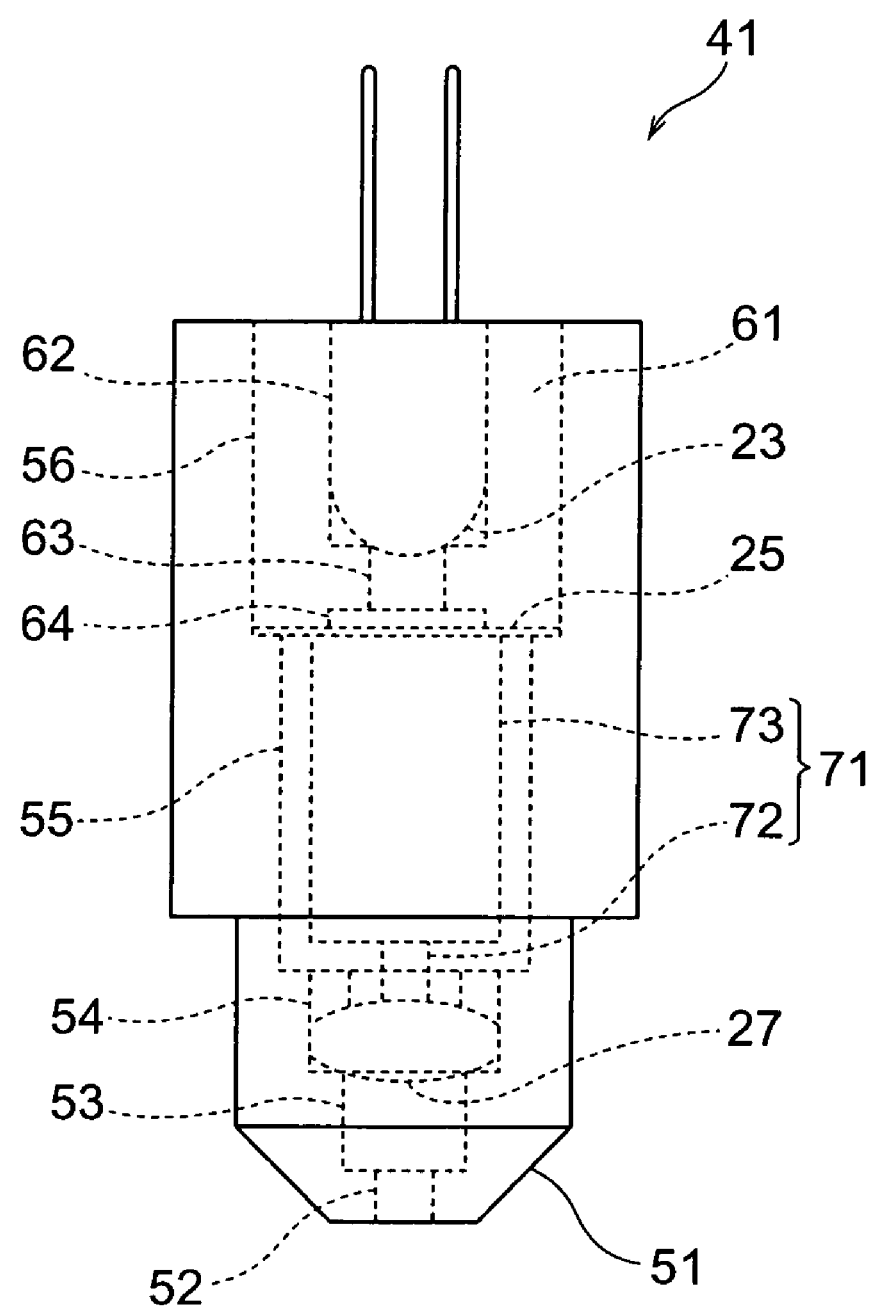
FIG. 4 is a side view of the optical head shown in FIGS. 1 and 2.
Figure 5:
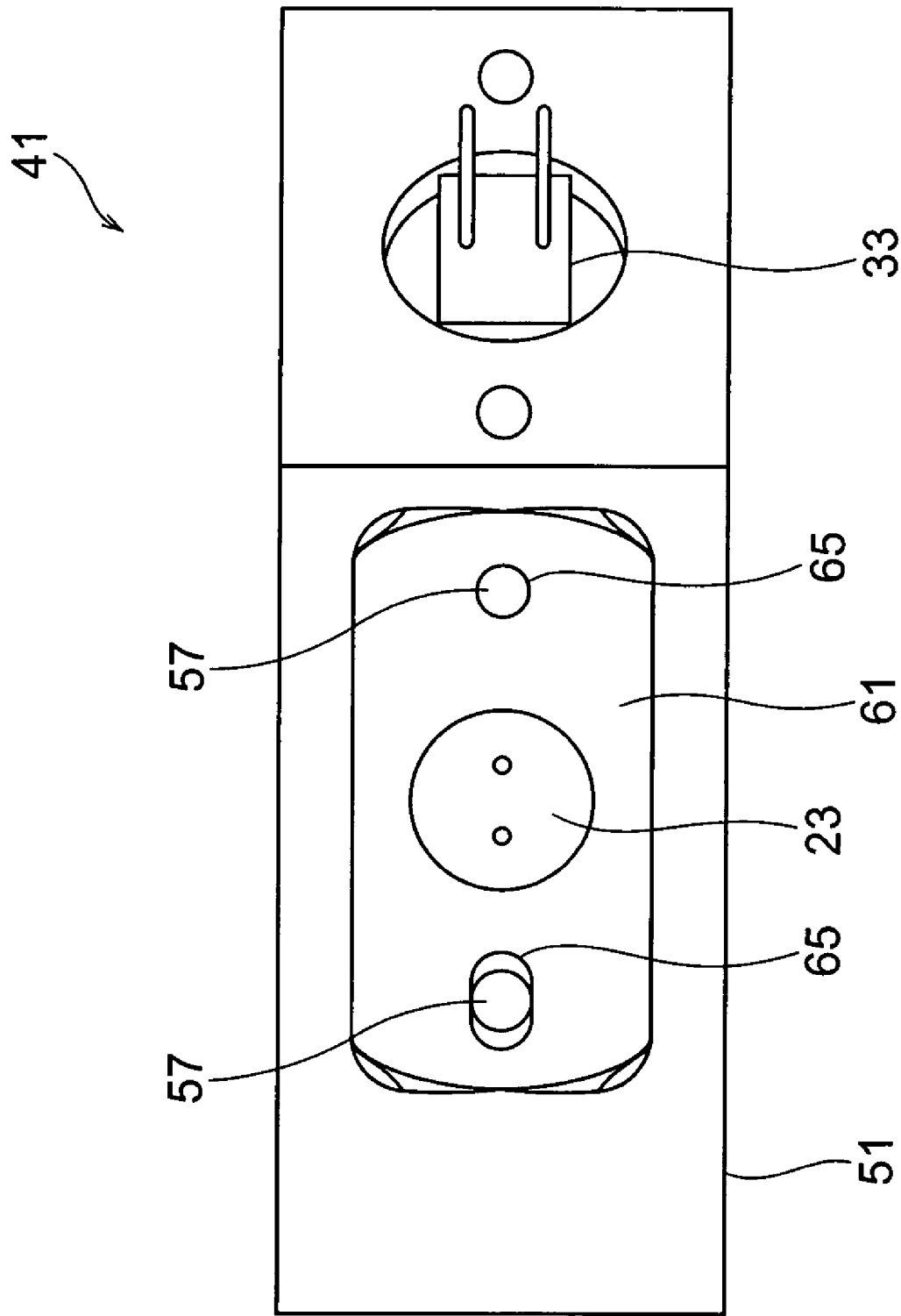
FIG. 5 is a plan view of the optical head shown in FIGS. 1 and 2.
Figure 6:
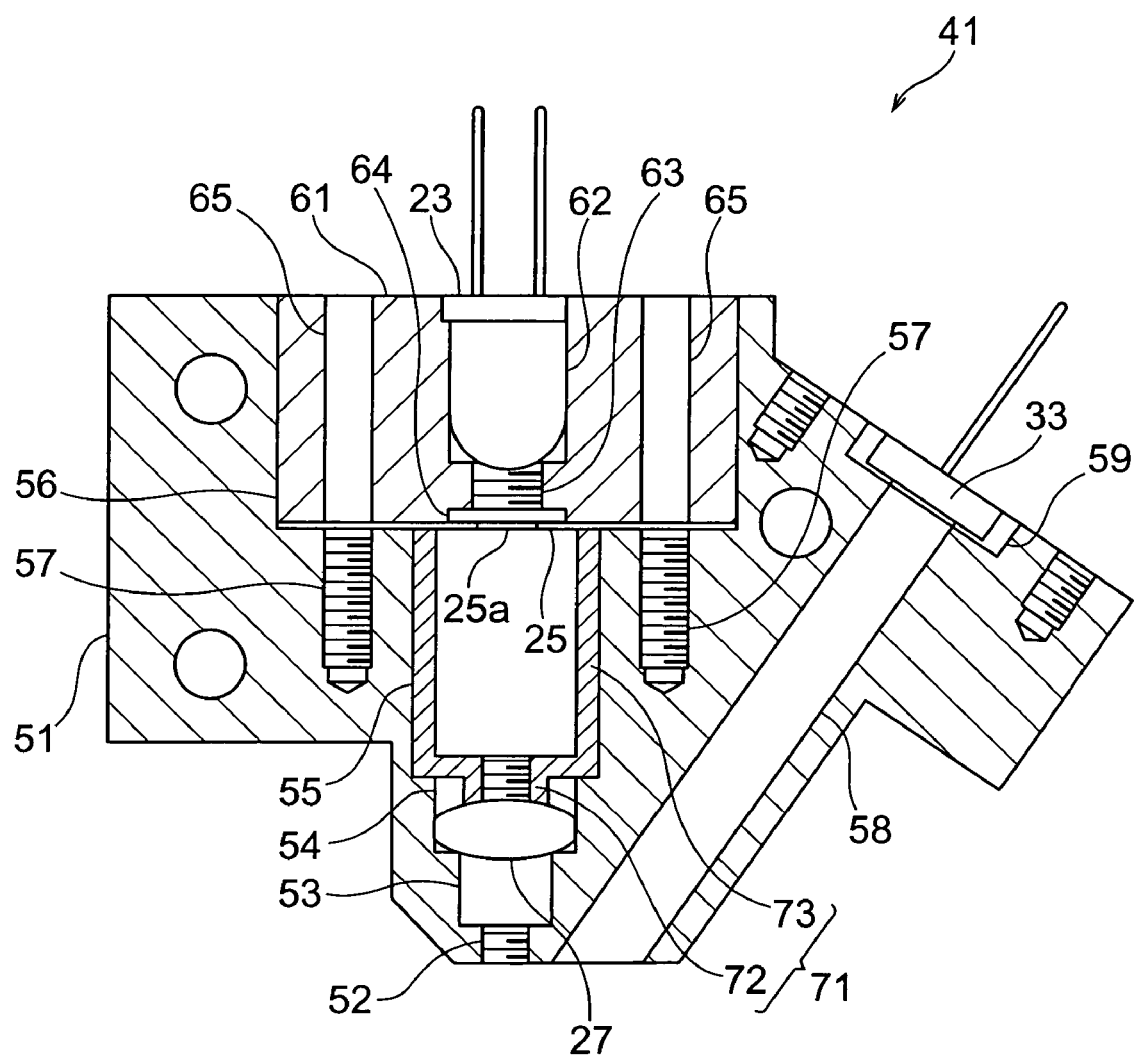
FIG. 6 is a sectional view of the optical head shown in FIGS. 1 and 2.
Figure 7:
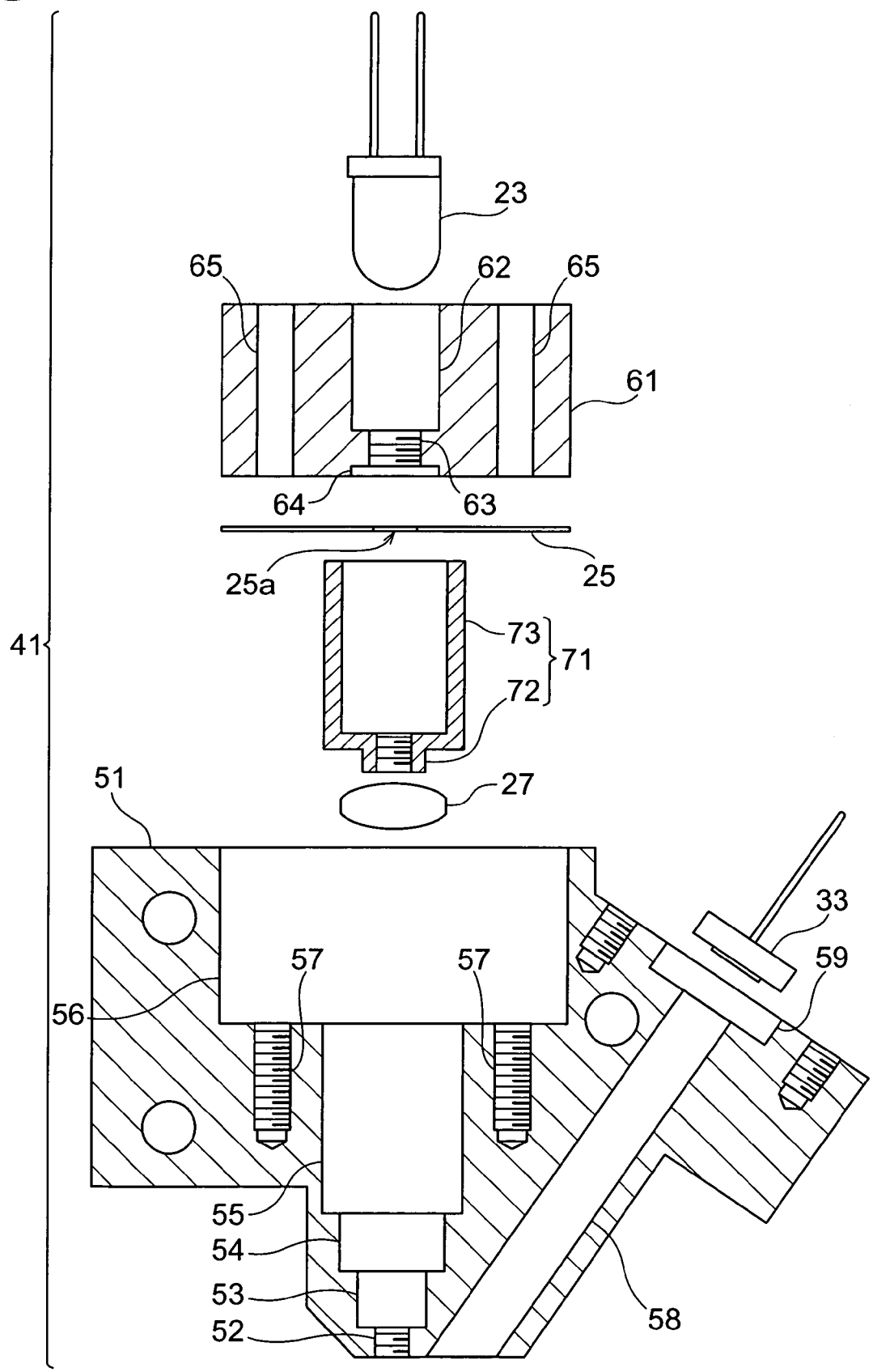
FIG. 7 is an exploded sectional view of the optical head shown in FIGS. 1 and 2.

The optical head 41, as shown in FIGS. 4 to 7, includes a first member 51, a second member 61, and a tubular member 71, and is supported above the immunochromatography test equipment TE while the upper part thereof is fixed through a support plate 14 to a slider block 13 forming the scanning mechanism 12. FIG. 4 is a side view of the optical head shown in FIGS. 1 and 2, FIG. 5 a plan view of the optical head shown in FIGS. 1 and 2, FIG. 6 a sectional view of the optical head shown in FIGS. 1 and 2, and FIG. 7 an exploded configuration diagram of the optical head shown in FIGS. 1 and 2.

The first member 51 has a first hole portion 52 of female screw shape having a predetermined inside diameter (e.g., about M2), a second hole portion 53 having an inside diameter (e.g., about φ4 mm) larger than that of the first hole portion 52, a third hole portion 54 having an inside diameter (e.g., about φ6 mm) larger than that of the second hole portion 53, a fourth hole portion 55 (e.g., a square hole 6.8 mm long) having an inside diameter larger than that of the third hole portion 54, and a fifth hole portion 56 (e.g., a square hole 15 mm long) having an inside diameter larger than that of the fourth hole portion 55, these hole portions being continuously formed so as to penetrate the first member 51. Bolt holes 57 to mesh with bolts for fixing the second member 61 are formed in the first member 51. The first member 51 is so located that the first hole portion 52 is positioned on the placing plate 11 (immunochromatography test equipment TE) side and that the center axis of the first to fifth hole portions 52–56 is nearly perpendicular to the placing plate 11 (immunochromatography test piece 1). The lens 27 is fit in the third hole portion 54.

The second member 61 has a cross section of square shape when cut by a plane normal to the optical axis of the semiconductor light emitting element 23, and has a sixth hole portion 62, a seventh hole portion 63, and an eighth hole portion 64 continuously formed so as to penetrate the second member 61. Through holes 65 for penetration of bolts are formed in the second member 61. This second member 61 is housed in the fifth hole portion 56 of the first member 51 and fixed to the first member 51 by bolts. The semiconductor light emitting element 23 is set in the sixth hole portion 62. The inside diameter of the seventh hole portion 63 is set to a predetermined value in female screw shape (e.g., about M3), and the inside diameter of the eighth hole portion 64 to a value (e.g., about φ5 mm) larger than the inside diameter of the seventh hole portion 63. Although the fifth hole portion 56 of the first member 51 is formed as a hole of square shape corresponding to the shape of the second member 61, the shape of the fifth hole portion 56 does not have to be limited to this example, but may be any shape (e.g., circular shape) as long as it corresponds to the shape of the second member 61 and allows the second member 61 to be inserted therein.

The tubular member 71 has a first tube portion 72 having a predetermined inside diameter (e.g., about M2) in female screw shape on one end side, and a second tube portion 73 having an inside diameter (e.g., about φ5 mm) larger than that of the first tube portion 72, on the other end side. The tubular member 71 is housed in the fourth hole portion 55 of the first member 51. The tubular member 71 has a cross section of square outside shape when cut by a plane normal to the optical axis of the semiconductor light emitting element 23. Although the fourth hole portion 55 of the first member 51 is formed as a hole of square shape corresponding to the shape of the tubular member 71, the shape of the fourth hole portion 55 does not have to be limited to this but may be any shape (e.g., circular shape) as long as it corresponds to the shape of the tubular member 71 and allows the tubular member 71 to be set therein.

In assembly of the elements of the irradiation optical system 21 into the first member 51, the lens 27 is first inserted into the third hole portion 54 and thereafter the tubular member 71 is inserted into the fourth hole portion 55. Subsequently, the beam shaping member 25 is mounted on a step portion formed at a border portion between the fourth hole portion 55 and the fifth hole portion 56, and the second member 61 is inserted into the fifth hole portion 56. Then the semiconductor light emitting element 23 supported on a substrate (not shown) is inserted into the sixth hole portion 62 and thereafter the substrate and second member 61 are fixed to the first member 51 with bolts. At this time, the lens 27 is sandwiched and fixed between the first tube portion 72 of the tubular member 71 and a step portion formed at a border portion between the second hole portion 53 and the third hole portion 54 of the first member 51. The beam shaping member 25 is sandwiched and fixed between the second member 61 and a step portion formed at a border portion between the fourth hole portion 55 and the fifth hole portion 56 of the first member 51.

Figure 8:
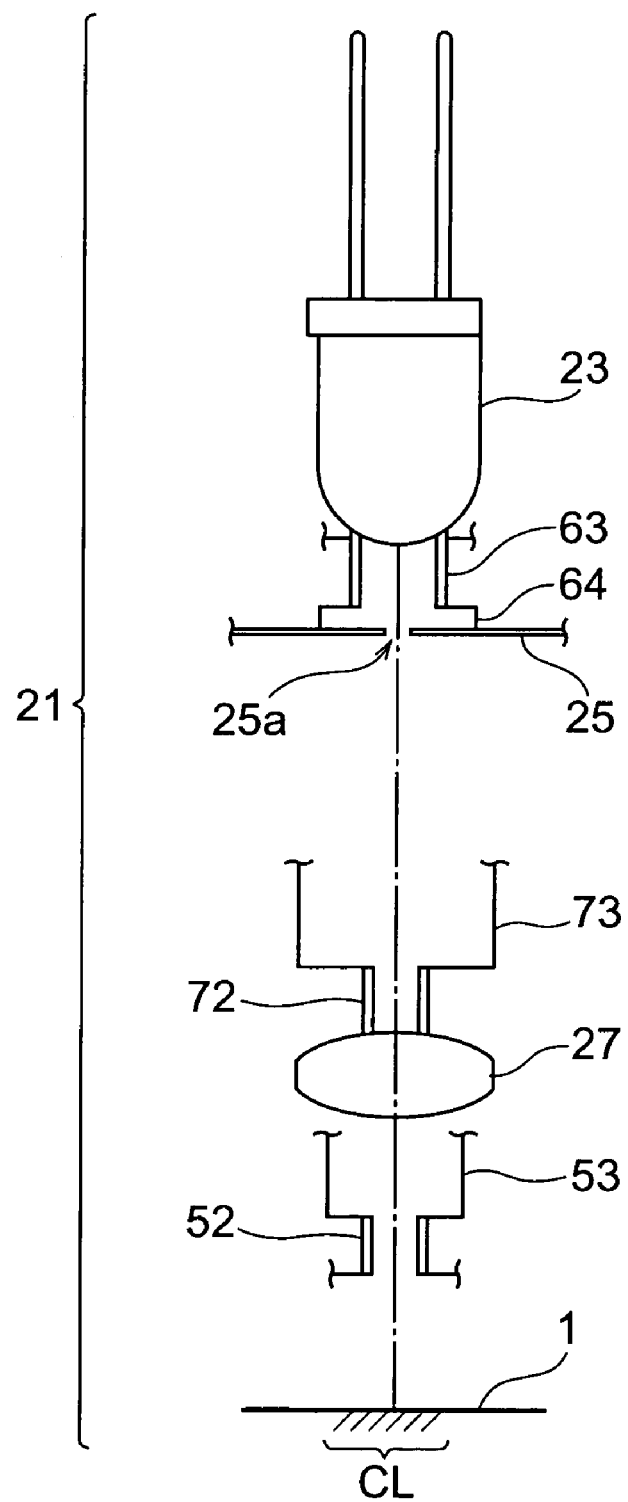
FIG. 8 is a schematic illustration for explaining a configuration of an irradiation optical system included in the measuring device for immunochromatography test piece according to the embodiment.

The light emitted from the semiconductor light emitting element 23, as also shown in FIG. 8, travels in order from the side of semiconductor light emitting element 23, through the seventh hole portion 63 and the eighth hole portion 64 of the second member 61, the slit 25a, the second tube portion 73 and the first tube portion 72 of the tubular member 71, the lens 27, and the second hole portion 53 and the first hole portion 52 of the first member 51 to be shaped into a slit beam nearly parallel to the colored line CL formed on the immunochromatography test piece 1, and the slit beam is projected from a direction nearly perpendicular to the immunochromatography test piece 1, onto the immunochromatography test piece 1. At this time, the seventh hole portion 63 is located between the semiconductor light emitting element 23 and the beam shaping member 25 to function as a first baffle portion of tubular shape for removing stray light. The first tube portion 72 is located between the beam shaping member 25 and the lens 27 to function as a second baffle portion of tubular shape for removing stray light. The first hole portion 52 is located between the lens 27 and the immunochromatography test piece 1 to function as a third baffle portion of tubular shape for removing stray light. A space portion defined by the eighth hole portion 64 is located between the seventh hole portion 63 (first baffle portion) and the beam shaping member 25 to function as a tubular space portion with a diameter larger than that of the seventh hole portion 63. A space portion defined by the second tube portion 73 is located between the beam shaping member 25 and the first tube portion 72 (second baffle portion) to function as a tubular space portion with a diameter larger than the inside diameter of the first tube portion 72. A space portion defined by the second hole portion 53 is located between the lens 27 and the first hole portion 52 (third baffle portion) to function as a tubular space portion with a diameter larger than that of the first hole portion 52.

The first member 51 has a ninth hole portion 58 having a predetermined inside diameter (e.g., about ϕ3.2 mm), and a tenth hole portion 59 having an inside diameter (e.g., about ϕ8 mm) larger than that of the ninth hole portion 58, the hole portions 58 and 59 being continuously formed so as to penetrate the first member 51. The ninth hole portion 58 is located on the side of placing plate 11 (immunochromatography test equipment TE). The ninth hole portion 58 has its lower end juxtaposed to the first hole portion 52 in the direction nearly parallel to the colored line CL formed on the immunochromatography test piece 1, and the ninth hole portion 58 extends obliquely upward from the lower end along the direction nearly parallel to the colored line CL.

The semiconductor photodetector 33 is set in the tenth hole portion 59. The semiconductor photodetector 33 is supported on a substrate (not shown), and the substrate is bolted and fixed to the first member 51 in a state in which the semiconductor photodetector 33 is inserted in the tenth hole portion 59. By this, the semiconductor photodetector 33 is provided at an obliquely upward position in the direction nearly parallel to the colored line CL formed on the immunochromatography test piece 1 with respect to the position of irradiation of the measurement light on the immunochromatography test piece 1, and detects obliquely upward reflected light in the direction nearly parallel to the colored line CL. The ninth hole portion 58 removes stray light generated from collision with the casing 3 of the immunochromatography test equipment TE and functions as a collimator for collimating the reflected light.

The scanning mechanism 12, as shown in FIG. 1, is mainly comprised of a pair of left and right guide rails 15 for slidably guiding the slider block 13 in the longitudinal direction of the placing plate 11, i.e., in the scan direction perpendicularly traversing the colored line CL formed on the immunochromatography test piece 1, a pinion 17 meshing with a rack 16 formed on a side face of the slider block 13 and along the longitudinal direction of the guide rails 15, and a drive motor 19 to which a worm gear 18 meshing with the pinion 17 is fixed.

In this scanning mechanism 12, as the worm gear 18 is rotated in a normal rotation direction by the drive motor 19, the pinion 17 is rotated as decelerated, and the slider block 13 with its rack 16 meshing with this pinion 17 moves in the scan direction while being guided by the pair of left and right guide rails 15. As a result, the optical head 41 moves relative to the placing plate 11 in the scan direction perpendicularly traversing the colored line CL formed on the immunochromatography test piece 1. Namely, the scan direction of the optical head 41 crosses the extending direction of the colored line CL formed on the immunochromatography test piece 1 placed on the placing plate 11. The extending direction of the slit 25a crosses the scan direction of the optical head 41 (in the present embodiment, they are perpendicular to each other), and the beam shaping member 25 shapes the light from the semiconductor light emitting element 23, into a beam of a beam section extending in the direction crossing the scan direction of the optical head 41.

Figure 9:
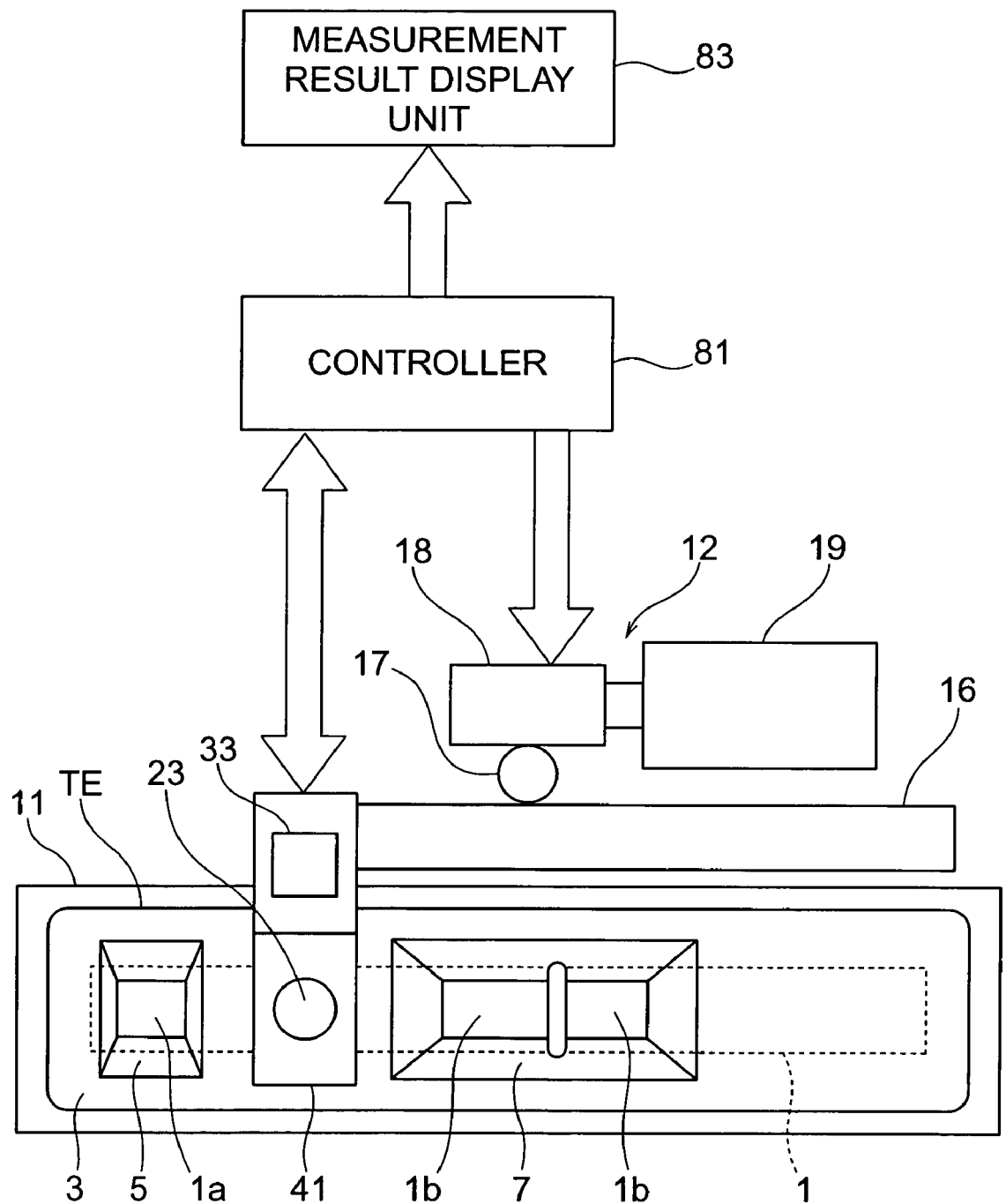
FIG. 9 is a system configuration diagram of the measuring device for immunochromatography test piece according to the embodiment.

The measuring device MD has a controller 81 and a measurement result display unit 83 as shown in FIG. 9, for control of rotation of the drive motor 19 in the scanning mechanism 12, for control of lighting of the semiconductor light emitting element 23, for processing of a received light signal from the semiconductor photodetector 33, and for display of processing result thereof. FIG. 9 is a system configuration diagram of the measuring device for immunochromatography test piece according to the present embodiment.

The controller 81 performs rotation control of normal rotation, stop, and backward rotation of the drive motor 19 in the scan mechanism 12, and lights up the semiconductor light emitting element 23 during movement of the optical head 41 in the scan direction with normal rotation of the drive motor 19 to project the measurement light (slit beam) onto the detection portion 1b of the immunochromatography test piece 1 exposed in the observation window 7 of the casing 3.

The controller 81 also takes in a detection signal from the semiconductor photodetector 33 receiving the reflected light from the detection portion 1b of the immunochromatography test piece 1 with lighting of the semiconductor light emitting element 23 and, for example, creates an absorption profile of the measurement light, based on the detection signal. Then the controller 81 calculates absorbance ABS of the colored line CL colored on the immunochromatography test piece 1, from the created absorption profile according to operational expression (1) below.

$$ABS = \log Ti/To \qquad (1)$$

Here To represents the intensity of the output signal of reflected light from the colored line CL and Ti the intensity of the output signal of reflected light from a non-colored portion.

Then the controller 81 refers to a calibration curve diagram prepared in advance, to determine the total amount (concentration) of the antigen (or antibody) included in the analyte according to the calculated absorbance ABS, and makes the measurement result display unit 83 display it.

For measuring the color intensity of the immunochromatography test piece 1 with the measuring device MD for immunochromatography test piece 1 having the above-described structure, the immunochromatography test equipment TE (cf. FIG. 3) is first prepared, and an analyte is delivered dropwise through the analyte drop window 5 of the casing 3 onto the analyte drop portion 1a of the immunochromatography test piece 1. This causes the analyte to develop toward the detection portion 1b of the immunochromatography test piece 1, and an antigen (or antibody) in the analyte brings about an antigen-antibody reaction with an antibody (or antigen) of a bandlike coating on the detection portion 1b to be trapped, thereby forming a colored line CL colored by the dye.

After the preparation as described above, as shown in FIG. 1, the immunochromatography test equipment TE is placed on the placing plate 11, and the controller 81 (cf. FIG. 9) lights up the semiconductor light emitting element 23 and rotates the drive motor 19 in the normal rotation direction. In conjunction with this operation, the slit beam nearly parallel to the colored line CL formed on the immunochromatography test piece 1 is projected onto the detection portion 1b of the immunochromatography test piece 1 through the observation window 7 of the casing 3 and the optical head 41 starts moving along the scan direction to move the slit light image in the scan direction on the detection portion 1b of the immunochromatography test piece 1. Then the semiconductor photodetector 33 receives obliquely upward reflected light in the direction nearly parallel to the colored line CL formed on the immunochromatography test piece 1, out of the reflected light from the detection portion 1b of the immunochromatography test piece 1, and outputs a detection signal to the controller 81.

Figure 10:
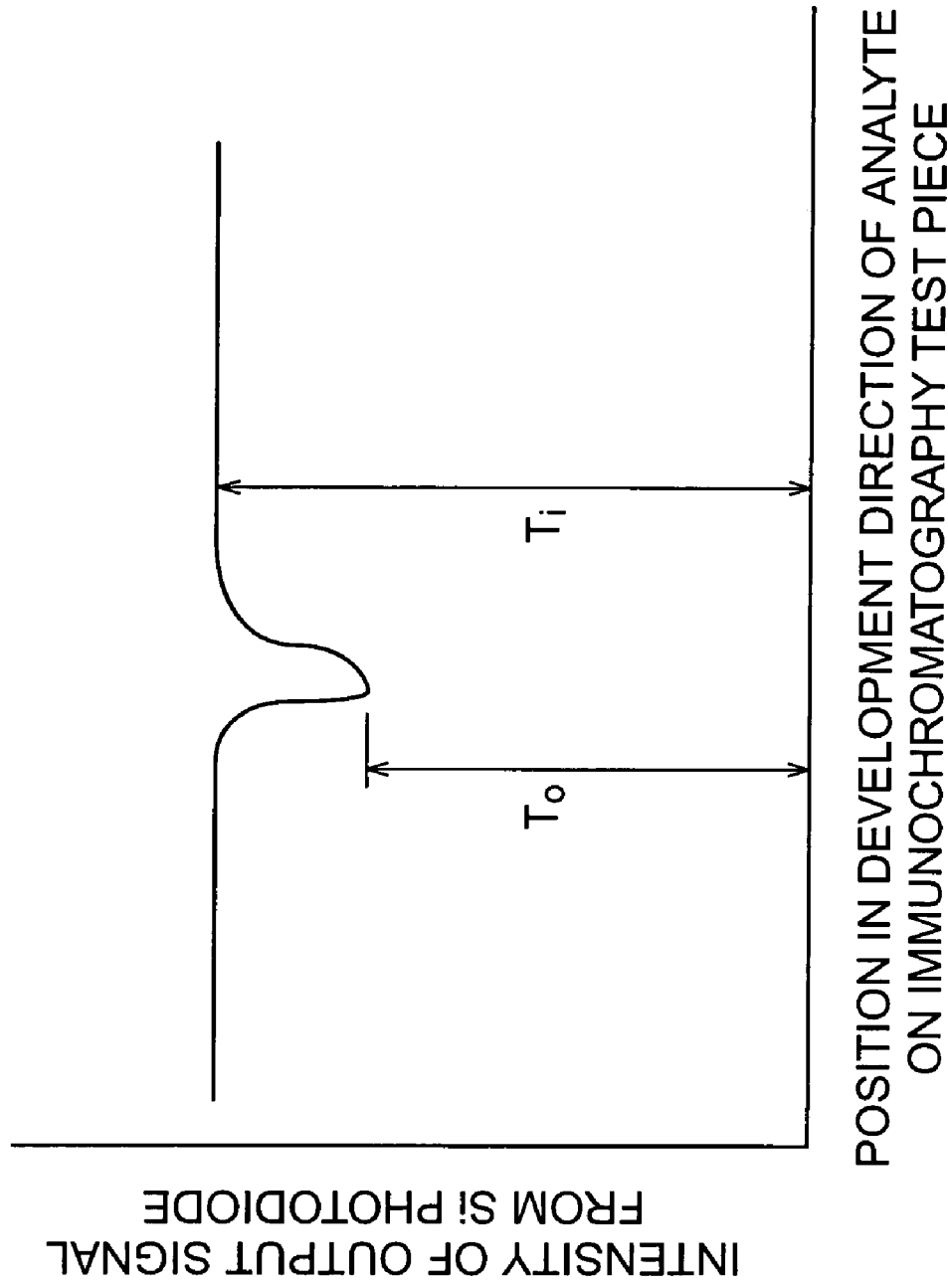
FIG. 10 is a diagram showing an absorption profile of transmitted light by an immunochromatography test piece included in the immunochromatography test equipment shown in FIG. 3.

The controller 81, receiving the detection signal, creates an absorption profile of the measured light, for example, as shown in FIG. 10, and calculates the absorbance ABS of the colored line CL on the immunochromatography test piece 1 from this absorption profile according to the aforementioned operational expression (1). Then the controller 81 refers to the calibration curve diagram prepared in advance, to determine the total amount (concentration) of the antigen (or antibody) included in the analyte according to the calculated absorbance ABS, and makes the measurement result display unit 83 display it.

In this manner, the measuring device MD of the present embodiment measures the color intensity of the colored line CL formed in the detection portion 1b of the immunochromatography test piece 1 housed in the casing 3.

In the present embodiment, as described above, the seventh hole portion 63 (first baffle portion) is located between the semiconductor light emitting element 23 and the beam shaping member 25, the first tube portion 72 (second baffle portion) of the tubular member 71 between the beam shaping member 25 and the lens 27, and the first hole portion 52 (third baffle portion) between the lens 27 and the immunochromatography test piece 1 (placing plate 11); therefore, these hole portions and tube portion suppress the generation of stray light. The lens 27 focuses the light (slit beam) from the beam shaping member 25 on the immunochromatography test piece 1. These result in suppressing the incidence of unwanted stray light to the immunochromatography test piece 1, so as to sharpen the measurement light (slit beam) projected onto the immunochromatography test piece 1, whereby it is feasible to achieve significant improvement in the measurement accuracy of color intensity.

Incidentally, the colored line CL can have color heterogeneity in the extending direction of the colored line CL. In the present embodiment, however, the irradiation optical system 21 irradiates the slit light extending in the direction nearly parallel to the colored line CL so as to be superimposed on the colored line CL; therefore, even if there occurs color heterogeneity, the color heterogeneity will be optically averaged and the reflected light resulting from the optical averaging of color heterogeneity will enter the semiconductor photodetector 33, whereby the color intensity of the immunochromatography test piece 1 can be measured with accuracy.

In the present embodiment, the optical head 41 has the eighth hole portion 64 with the diameter larger than that of the seventh hole portion 63, which is disposed between the seventh hole portion 63 and the beam shaping member 25. By this, the irradiation optical system 21 is constructed to have the space portion (tubular space portion) defined by the eighth hole portion 64. As a result, stray light is confined in the space portion defined by the eighth hole portion 64, whereby it is feasible to further suppress the incidence of unwanted stray light to the immunochromatography test piece 1.

In the present embodiment, the optical head 41 has the second tube portion 73 with the inside diameter larger than that of the first tube portion 72, which is disposed between the beam shaping member 25 and the first tube portion 72 of the tubular member 71. By this, the irradiation optical system 21 is constructed to have the space portion (tubular space portion) defined by the second tube portion 73. This results in confining stray light in the space portion defined by the second tube portion 73, whereby it is feasible to further suppress the incidence of unwanted stray light to the immunochromatography test piece 1.

In the present embodiment, the optical head 41 has the second hole portion 53 with the diameter larger than that of the first hole portion 52, which is disposed between the lens 27 and the first hole portion 52. By this, the irradiation optical system 21 is constructed to have the space portion (tubular space portion) defined by the second hole portion 53. This results in confining stray light in the space portion defined by the second hole portion 53, whereby it is feasible to further suppress the incidence of unwanted stray light to the immunochromatography test piece 1.

In the present embodiment, the irradiation optical system 21 is mounted on the optical head 41, and the optical head 41 includes the first member 51 having the first hole portion 51, second hole portion 53, third hole portion 54, fourth hole portion 55, and fifth hole portion 56 continuously formed, the second member 61 housed inside the fifth hole portion 56 and having the sixth hole portion 62 and seventh hole portion 63 continuously formed, and the tubular member 71 housed in the fourth hole portion 55. Then the lens 27 is fixed by the tubular member 71 and the step portion formed at the border portion between the second hole portion 53 and the third hole portion 54, and the beam shaping member 25 is fixed by the second member 61 and the step portion formed at the border portion between the fourth hole portion 55 and the fifth hole portion 56. This enables the irradiation optical system 21 to be incorporated in the optical head 41 to be unitized, which achieves simplification of the structure and which facilitates the assembly of the semiconductor light emitting element 23, beam shaping member 25, and lens 27.

In the present embodiment, a female screw is formed in each inside surface of the first hole portion 52, the seventh hole portion 63, and the first tube portion 72 of the tubular member 71. This makes it feasible to further effectively suppress the incidence of unwanted stray light to the immunochromatography test piece 1, by the extremely simple configuration of formation of the female screw.

In the present embodiment, the measuring device MD has the optical head 41 on which the irradiation optical system 21 and detection optical system 31 are placed, the placing plate 11 for placing of the immunochromatography test equipment TE (immunochromatography test piece 1), and the scanning mechanism 12 for effecting relative movement between the optical head 41 and the placing plate 11 in the scan direction traversing the colored line CL. In this configuration, the irradiation optical system 21 and detection optical system 31 are mounted on the optical head 41, which simplifies the structure and which requires only one system as the scanning mechanism 12 for moving the optical head 41 in the scan direction, thus simplifying the structure of the scanning mechanism 12 and the configuration of the control system thereof.

In the present embodiment, the light emitting diode is used as the semiconductor light emitting element 23. This permits us to increase the intensity of light from the light source.

In the present embodiment, the beam shaping member 25 is a platelike member with the slit 25a extending in the direction nearly parallel to the colored line CL formed on the immunochromatography test piece 1, i.e., stretching in the direction crossing the scan direction of the optical head 41. This simplifies the structure of the beam shaping member 25.

Figure 11:
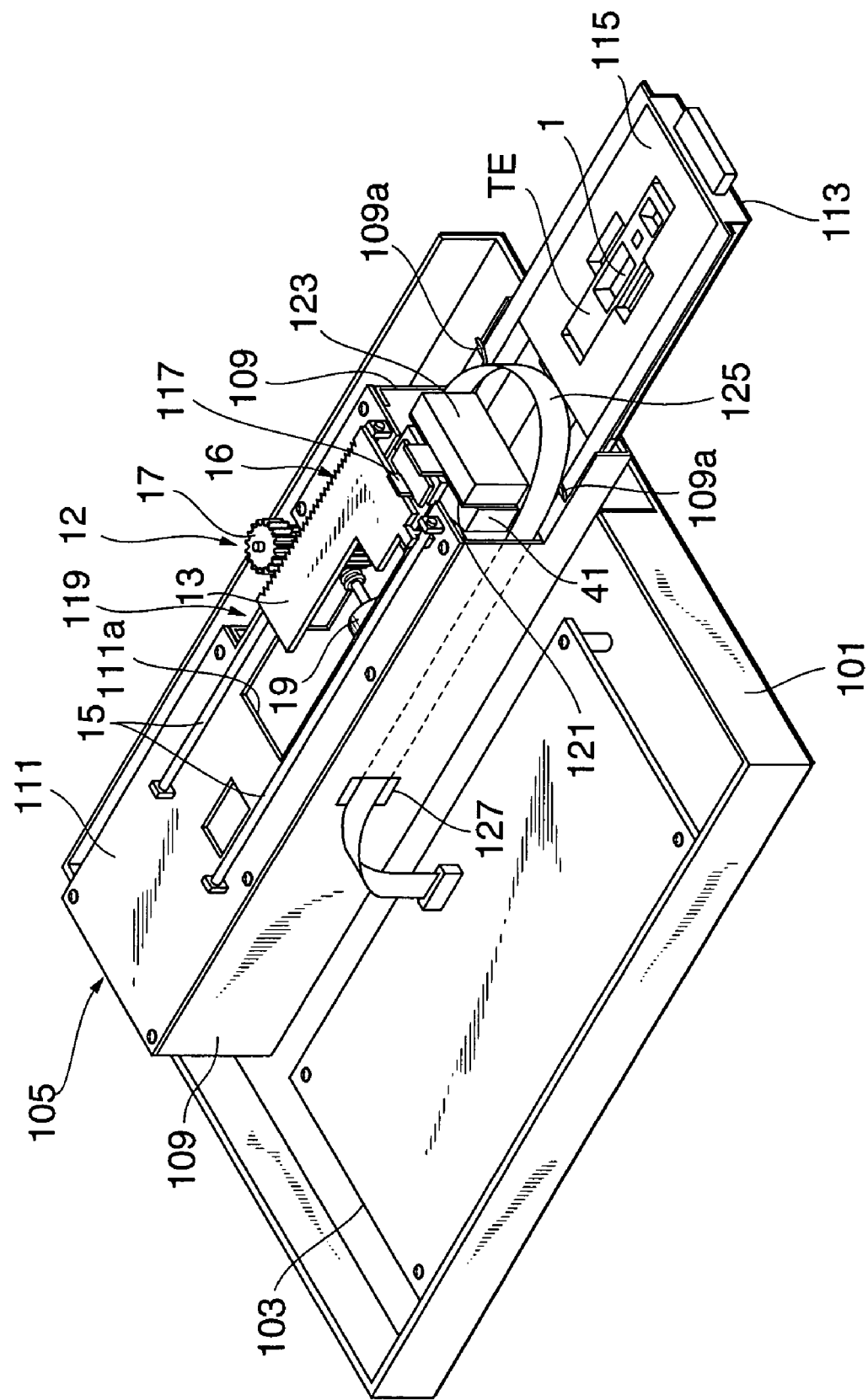
FIG. 11 is a perspective view showing a modification example of the measuring device for immunochromatography test piece according to the embodiment.
Figure 12:
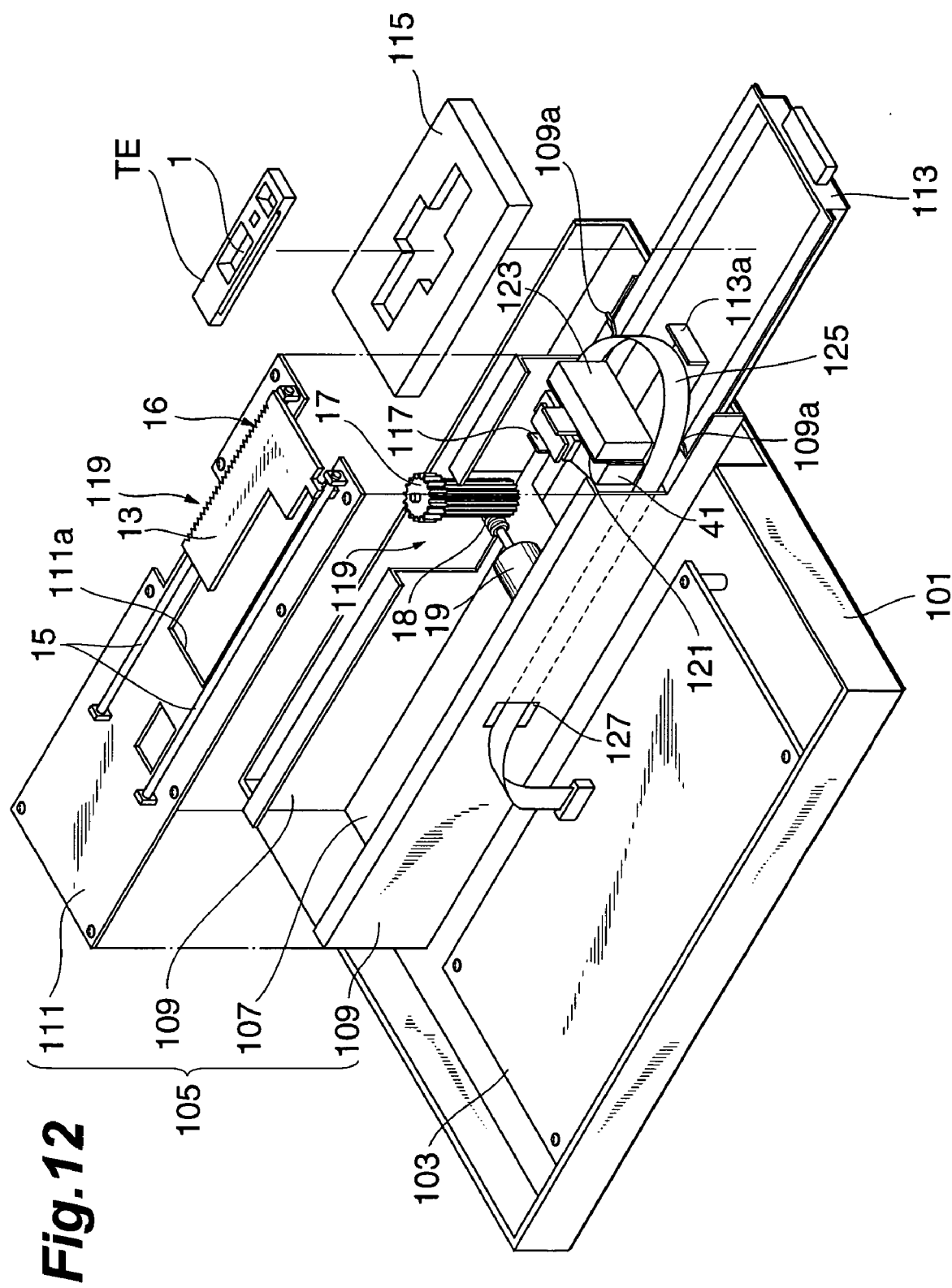
FIG. 12 is an exploded perspective view showing the modification example of the measuring device for immunochromatography test piece according to the embodiment.
Figure 13:
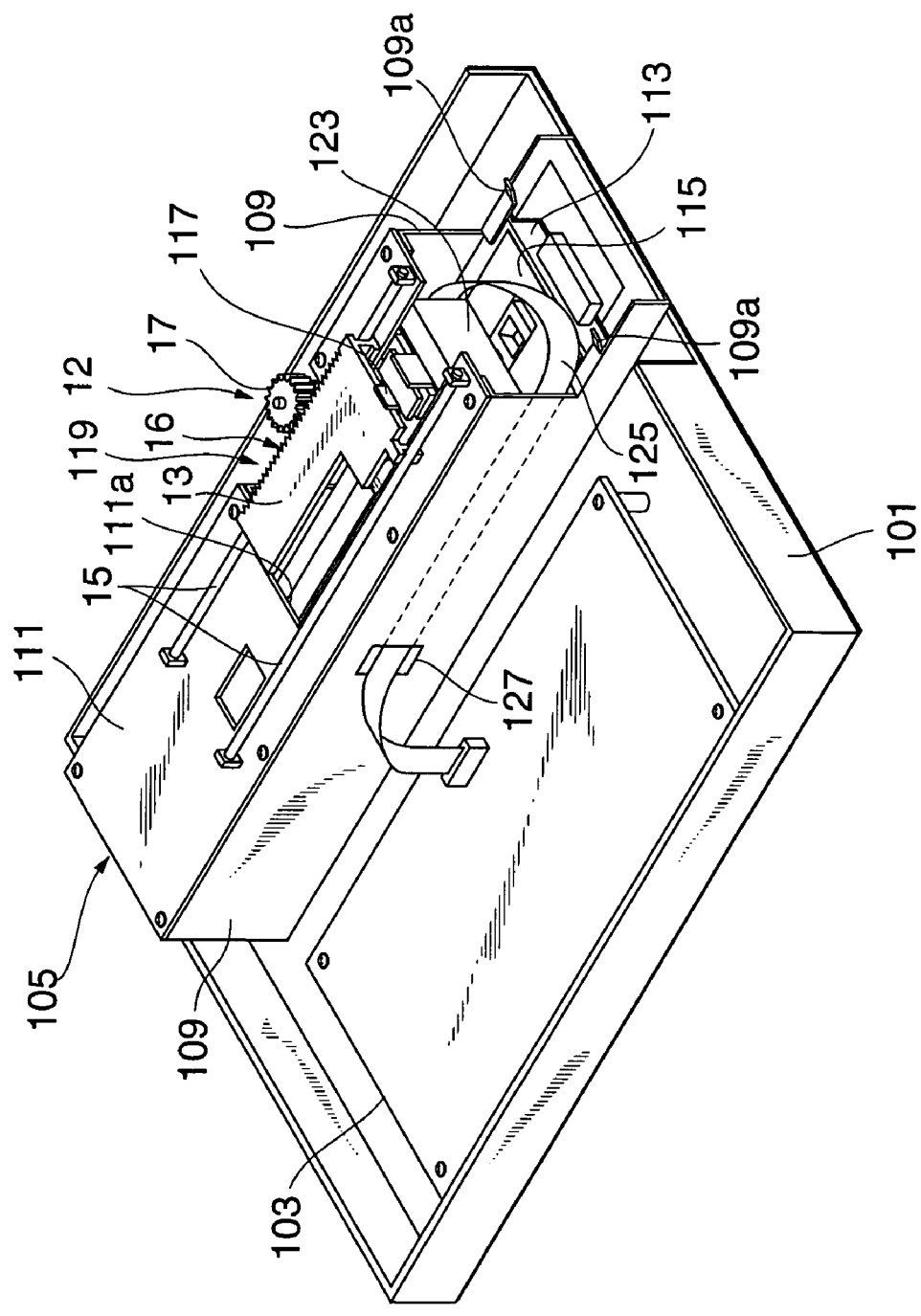
FIG. 13 is a perspective view showing the modification example of the measuring device for immunochromatography test piece according to the embodiment.
Figure 14:
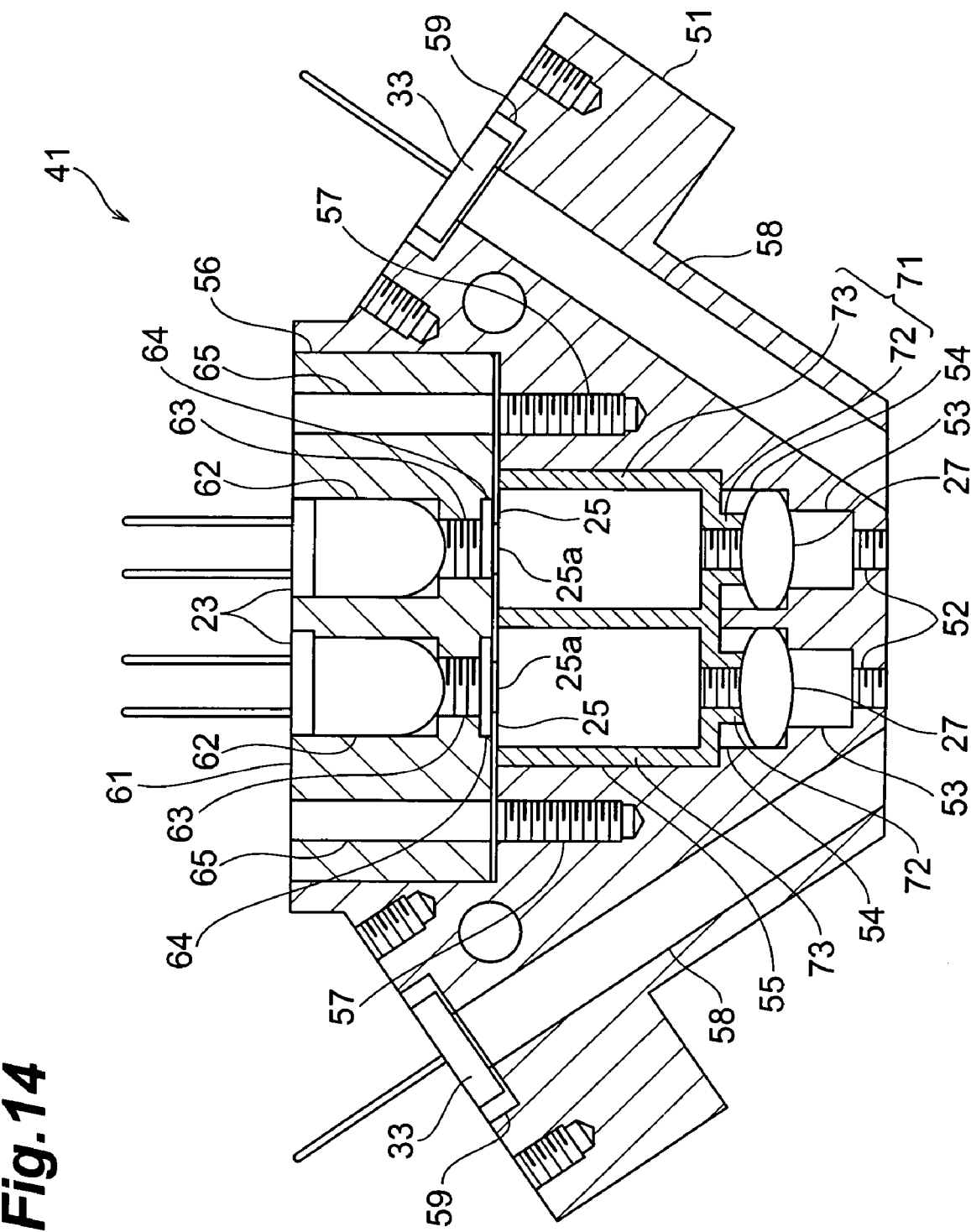
FIG. 14 is a sectional view of the optical head shown in FIGS. 11 to 13.

Next, a modification example of the measuring device MD of the above embodiment will be described with reference to FIGS. 11 to 14. FIG. 11 and FIG. 13 are perspective views showing the modification example of the measuring device for immunochromatography test piece of the embodiment. FIG. 12 is an exploded perspective view showing the modification example of the measuring device for immunochromatography test piece of the embodiment. FIG. 14 is a sectional view of the optical head shown in FIGS. 11 to 13.

The measuring device MD of the modification example is provided with a housing (not shown) of box shape opening in its bottom face, and a base plate 101 to close the opening of the housing. Fixed to the base plate 101 are a first board 103 equipped with a CPU and others constituting the aforementioned controller 81, and a chassis 105 on which the scanning mechanism 12 is placed. The chassis 105 is of tubular shape with an almost rectangular cross section, and includes a bottom portion 107 located opposite to the base plate 101, a pair of vertical wall portions 109 extending from the both edges of the bottom portion 107, and a top portion 111 opposed to the bottom portion 107 and coupled to each vertical wall portion 109. The top portion 111 is detachably attached to the vertical wall portions 109.

On the chassis 105, a tray 113 is placed so as to be slidable in the longitudinal direction of the chassis 105. The vertical wall portions 109 are located on both sides of the tray 113 with the tray 113 in between. FIG. 11 and FIG. 12 show a state in which the tray 113 is drawn out of the chassis 105, and FIG. 13 shows a state in which the tray 113 is brought into the chassis 105. A holder 115 for holding the immunochromatography test equipment TE is placed on the tray 113.

The tray 113 is detachable from the chassis 105 and functions as a pedestal on which the immunochromatography test piece 1 is placed. The tray 113 is provided with a positioning piece 113a for positioning the holder 115. Each of the vertical wall portions 109 is provided with a regulation piece 109a for properly sliding the tray 113. In a state in which the tray 113 loaded with the holder 115 holding the immunochromatography test equipment TE is set in the chassis 105, the tray 113 and immunochromatography test equipment TE are surrounded by the vertical wall portions 109 and top portion 111. This prevents light from the outside of the chassis 105 from entering the immunochromatography test equipment TE (immunochromatography test piece 1), whereby it is feasible to achieve significant improvement in the measurement accuracy of color intensity of the immunochromatography test piece 1.

A cut 111a is formed in the top portion 111 so as to extend in the longitudinal direction of the chassis 105. A pair of guide rails 15 are fixed to the upper surface of the top portion 111 so as to interpose the cut 111a between them. The slider block 13 is located above the cut 111a and is movable in the extending direction of the cut 111a, i.e., in the longitudinal direction of the chassis 105. A bracket 117 for attachment of the optical head 41 is fixed to the slider block 13.

The drive motor 19 is placed inside the chassis 105. The pinion 17 is placed through a hole 119 formed in a region from the vertical wall portion 109 to the top portion 111, and the upper part thereof is located above the top portion 111. The upper part of the pinion 17 meshes with the rack 16 formed in the slider block 13. The lower part of the pinion 17 meshes with the worm gear 18 fixed to the rotational shaft of the drive motor 19.

The optical head 41 is fixed to the bracket 117 extending through the cut 111a. This permits the optical head 41 to move along the longitudinal direction of the chassis 105 and inside the chassis 105 with movement of the slider block 13. This prevents light from the outside of the chassis 105 from entering the semiconductor photodetector 33, whereby it is feasible to achieve significant improvement in the measurement accuracy of color intensity of the immunochromatography test piece 1. The scan direction of the optical head 41 coincides with the longitudinal direction of the chassis 105.

Fixed to the optical head 41 is a second board 121 in which a drive circuit for controlling emission of light from the semiconductor light emitting element 23 is formed. This second board 121 is protected by a metal cover 123. The first board 103 and second board 121 are electrically coupled to each other through a communication cable 125 with flexibility and elasticity.

The communication cable 125 is so routed that it runs through a hole 127 formed in one vertical wall portion 109, to the inside of the chassis 105, then extends in the longitudinal direction of the chassis 105 along one vertical wall portion 109 inside the chassis 105, and is curved from an edge of one vertical wall portion 109 to the other vertical wall portion 109 (second board 121) outside the chassis 105. The portion of the communication cable 125 located in the chassis 105 is fixed to one vertical wall portion 109 with an adhesive or the like. The length of the communication cable 125 from the part fixed to one vertical wall portion 109, to the second board 121 needs to be set in consideration of the moving distance of the optical head 41 (second board 121).

By this configuration wherein the communication cable 125 is placed through the interior of the chassis 105, the length of the communication cable 125 can be set as short as possible, and it can prevent a tangle, a bend, engulfment, and so on.

The optical head 41 in the modification example, as shown in FIG. 14, is provided with a pair of semiconductor light emitting elements 23 and a pair of semiconductor photodetectors 33. Namely, there are provided a pair of aforementioned irradiation optical systems and detection optical systems, which permits the measuring device to simultaneously measure color intensities of two immunochromatography test pieces set on one immunochromatography test equipment.

In the measuring device MD of the modification example, the slider block 13 and the pair of guide rails 15 are placed on the surface of the top portion 111 opposite the space surrounded by the pair of vertical wall portions 109 and top portion 111, and the top portion 111 is provided with the cut 111a extending in the scan direction of the optical head 41, at the position where the cut is interposed between the pair of guide rails 15. The optical head 41 and slider block 13 are coupled and fixed through the cut. This accomplishes the configuration wherein the optical head 41 is surely movable in the scan direction inside the chassis 105, i.e., in the space surrounded by the pair of vertical wall portions 109 and top portion 111, without difficulty and at low cost.

In the measuring devices MD of the above embodiment and the modification example thereof, the optical head 41 moves relative to the placing plate 11 or relative to the tray 113 in the scan direction. For this reason, the measuring devices MD are simpler in structure on the placing plate 11 or tray 113 side than the measuring devices of structure in which the placing plate 11 or tray 113 moves relative to the optical head 41 in the scan direction. In this configuration, even if the placing plate 11 or tray 113 is contaminated, it can be cleaned relatively easily. In consequence thereof, the measuring devices MD are also hygienically excellent.

In the measuring device MD of the modification example, the tray 113 is detachably attached to the chassis 105. This permits one to clean the tray 113 readily, so that the measuring device is hygienically further excellent.

The present invention is by no means intended to be limited to the above embodiments. For example, the semiconductor light emitting element 23 can be any other semiconductor light emitting element such as a laser diode, instead of the light emitting diode. The semiconductor photodetector 33 can be any other semiconductor photodetector such as a phototransistor or a CCD image sensor, instead of the Si photodiode.

In the embodiment, the aforementioned baffle portions are formed all in the female screw shape, but it is possible to adopt a variety of configurations, e.g., a flat plate with an inside diameter different from those of the hole portions and tube portions, as long as they can function as baffle portions.

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

What is claimed is:

1. A measuring device for immunochromatography test piece, comprising:
    an irradiation optical system for irradiating measurement light onto an immunochromatography test piece, and
    a detection optical system for detecting reflected light from the immunochromatography test piece under irradiation with the measurement light,
    wherein said irradiation optical system comprises:
        a semiconductor light emitting element;
        a beam shaping member for shaping light from the semiconductor light emitting element, into a beam of a beam section extending in a direction substantially parallel to a colored line formed on the immunochromatography test piece;
        a lens for focusing the beam from the beam shaping member on the immunochromatography test piece;
        a first baffle portion of tubular shape for removing stray light, which is disposed between the semiconductor light emitting element and the beam shaping member;
        a second baffle portion of tubular shape for removing stray light, which is disposed between the beam shaping member and the lens; and
        a third baffle portion of tubular shape for removing stray light, which is disposed between the lens and the immunochromatography test piece.

2. The measuring device for immunochromatography test piece according to claim 1, wherein the irradiation optical system further comprises a tubular space portion with a diameter larger than that of the first baffle portion, which is disposed between the first baffle portion and the beam shaping member.

3. The measuring device for immunochromatography test piece according to claim 1, wherein the irradiation optical system further comprises a tubular space portion with a diameter larger than that of the second baffle portion, which is disposed between the beam shaping member and the second baffle portion.

4. The measuring device for immunochromatography test piece according to claim 1, wherein the irradiation optical system further comprises a tubular space portion with a diameter larger than that of the third baffle portion, which is disposed between the lens and the third baffle portion.

5. The measuring device for immunochromatography test piece according to claim 1, further comprising:
    an optical head on which the irradiation optical system and the detection optical system are mounted;
    a placing plate for placing of the immunochromatography test piece; and
    a scanning mechanism for effecting relative movement between the placing plate and the optical head in a scan direction traversing the colored line.

6. The measuring device for immunochromatography test piece according to claim 1, wherein the semiconductor light emitting element is a light emitting diode.

7. The measuring device for immunochromatography test piece according to claim 1, wherein the beam shaping member is a plate-like member in which a slit extending in a direction substantially parallel to the colored line formed on the immunochromatography test piece is formed.

8. A measuring device for immunochromatography test piece, comprising:
    an irradiation optical system for irradiating measurement light onto an immunochromatography test piece, wherein said irradiation optical system comprises:
        a semiconductor light emitting element;
        a beam shaping member for shaping light from the semiconductor light emitting element, into a beam of a beam section extending in a direction substantially parallel to a colored line formed on the immunochromatography test piece;

a lens for focusing the beam from the beam shaping member on the immunochromatography test piece;

a first baffle portion of tubular shape for removing stray light, which is disposed between the semiconductor light emitting element and the beam shaping member;

a second baffle portion of tubular shape for removing stray light, which is disposed between the beam shaping member and the lens; and a third baffle portion of tubular shape for removing stray light, which is disposed between the lens and the immunochromatography test piece;

a detection optical system for detecting reflected light from the immunochromatography test piece under irradiation with the measurement light, and an optical head on which the irradiation optical system is mounted, wherein said optical head comprises:

a first member comprising a first hole portion, a second hole portion, a third hole portion, a fourth hole portion, and a fifth hole portion continuously formed, wherein the first hole portion has a predetermined inside diameter so as to function as said third baffle portion, the second hole portion has an inside diameter larger than that of the first hole portion, the third hole portion has an inside diameter larger than that of the second hole portion and allows said lens to be inserted therein, the fourth hole portion has an inside diameter larger than that of the third hole portion, and the fifth hole portion has an inside diameter larger than that of the fourth hole portion;

a second member inserted in the fifth hole portion and comprising a sixth hole portion and a seventh hole portion continuously formed, wherein the sixth hole portion allows the semiconductor light emitting element to be inserted therein and the seventh hole portion has a predetermined inside diameter so as to function as said first baffle portion; and a tubular member inserted in the fourth hole portion and having a predetermined inside diameter so that a one-end portion functions as said second baffle portion, wherein said lens is fixed by the tubular member and a step portion formed at a border portion between the second hole portion and the third hole portion, and wherein the beam shaping member is fixed by the second member and a step portion formed at a border portion between the fourth hole portion and the fifth hole portion.

9. The measuring device for immunochromatography test piece according to claim 8, wherein in the second member, an eighth hole portion having an inside diameter larger than that of the seventh hole portion is formed so as to be continuous with the seventh hole portion.

10. The measuring device for immunochromatography test piece according to claim 8, wherein said tubular member comprises an other-end portion having an inside diameter set larger than the inside diameter of said one-end portion.

11. The measuring device for immunochromatography test piece according to claim 8, wherein a female screw is threaded in each inside surface of the first hole portion, the seventh hole portion, and the one-end portion of the tubular member.

12. A light source device for irradiating slit light onto a measuring object, comprising:

a semiconductor light emitting element;

a beam shaping member for shaping light from the semiconductor light emitting element, into a slit beam;

a lens for focusing the beam from the beam shaping member on the measuring object;

a first baffle portion of tubular shape for removing stray light, which is disposed between the semiconductor light emitting element and the beam shaping member;

a second baffle portion of tubular shape for removing stray light, which is disposed between the beam shaping member and the lens; and a third baffle portion of tubular shape for removing stray light, which is disposed between the lens and the measuring object.

13. The light source device according to claim 12, further comprising a tubular space portion with a diameter larger than that of the first baffle portion, which is disposed between the first baffle portion and the beam shaping member.

14. The light source device according to claim 12, further comprising a tubular space portion with a diameter larger than that of the second baffle portion, which is disposed between the beam shaping member and the second baffle portion.

15. The light source device according to claim 12, further comprising a tubular space portion with a diameter larger than that of the third baffle portion, which is disposed between the lens and the third baffle portion.

16. A measuring device for immunochromatography test piece, comprising:

a pedestal on which an immunochromatography test piece is placed;

an irradiation optical system for irradiating measurement light toward the pedestal; and a detection optical system for detecting light incident from the pedestal side, wherein the irradiation optical system and the detection optical system are arranged to move relative to the pedestal in a predetermined scan direction, and wherein the irradiation optical system comprises:

a semiconductor light emitting element;

a beam shaping member for shaping light from the semiconductor light emitting element, into a beam of a beam section extending in a direction crossing the predetermined scan direction;

a lens for focusing the beam from the beam shaping member;

a first baffle portion of tubular shape for removing stray light, which is disposed between the semiconductor light emitting element and the beam shaping member;

a second baffle portion of tubular shape for removing stray light, which is disposed between the beam shaping member and the lens; and a third baffle portion of tubular shape for removing stray light, which is disposed between the lens and the pedestal.

* * * * *